(12) United States Patent
Storm

(10) Patent No.: US 8,750,958 B2
(45) Date of Patent: Jun. 10, 2014

(54) DISPOSABLE ELECTRODE PATCH

(75) Inventor: Hanne Storm, Oslo (NO)

(73) Assignee: MedStorm Innovation AS, Oslo (NO)

( * ) Notice: Subject to any disclaimer, the term of this patent is extended or adjusted under 35 U.S.C. 154(b) by 0 days.

(21) Appl. No.: 13/637,653

(22) PCT Filed: Apr. 8, 2010

(86) PCT No.: PCT/NO2010/000130
§ 371 (c)(1),
(2), (4) Date: Sep. 27, 2012

(87) PCT Pub. No.: WO2011/126376
PCT Pub. Date: Oct. 13, 2011

(65) Prior Publication Data
US 2013/0018249 A1    Jan. 17, 2013

(51) Int. Cl.
*A61B 5/04* (2006.01)
*A61B 5/0492* (2006.01)

(52) U.S. Cl.
USPC ............ 600/384; 600/390; 600/391; 600/393

(58) Field of Classification Search
USPC ......... 600/382, 384–386, 390, 393, 547, 391, 600/392
See application file for complete search history.

(56) References Cited

U.S. PATENT DOCUMENTS

| | | | |
|---|---|---|---|
| 6,577,897 B1 * | 6/2003 | Shurubura et al. | 600/547 |
| 6,865,409 B2 * | 3/2005 | Getsla et al. | 600/393 |
| D511,450 S * | 11/2005 | Seth | D8/396 |
| 7,738,939 B2 * | 6/2010 | Hallin | 600/393 |
| 8,208,985 B2 * | 6/2012 | Kim et al. | 600/393 |
| 2005/0277822 A1 * | 12/2005 | Manabe et al. | 600/393 |
| 2007/0100219 A1 * | 5/2007 | Sweitzer et al. | 600/323 |

FOREIGN PATENT DOCUMENTS

| | | |
|---|---|---|
| JP | 19950172040950707 | 1/1997 |
| JP | 19960235003960905 | 3/1998 |
| WO | 00/72751 | 12/2000 |
| WO | 2007/050268 | 5/2007 |

OTHER PUBLICATIONS

JP Office action of Feb. 4, 2014, with machine translation, submitted inter alia as statement of relevance of cited non-English references (together with English abstacts of said references).

* cited by examiner

*Primary Examiner* — Lee S Cohen
(74) *Attorney, Agent, or Firm* — Christian D. Abel

(57) ABSTRACT

A disposable electrode patch for medical purposes comprises a flexible, elongated substrate with a first and a second surface, a first adhesive material disposed on a first adhesive area at a first end of the first surface, and a second adhesive material disposed on a second adhesive area at a second end of the first surface. Electrodes are arranged between the first and second adhesive areas on the first surface of the substrate. In use, the electrode patch is folded around a body part in such a way that the electrodes on the first surface make contact with the skin of the body part, while the first and second adhesive areas of the first surface are pinched together to form a stable assembly surrounding the body part.

6 Claims, 2 Drawing Sheets

DISPOSABLE ELECTRODE PATCH

FIELD OF THE INVENTION

The invention relates to a disposable electrode patch for medical purposes, particularly to be fixed onto the skin of a body part of a patient.

BACKGROUND OF THE INVENTION

Medical electrodes are needed in many applications, e.g. for measurement of electrical activity in the brain (EEG), the heart (ECG), or the muscles (EMG). Medical electrodes may be used for measuring, e.g., electric current, potential/voltage, skin conductance, and skin resistance. Certain medical electrodes may also be used for supplying electrical energy into the patient, e.g. in the case of defibrillators, electroconvulsive therapy and other therapy methods.

Medical electrodes are also used in the fields of electrophysiology and neuroscience. A particular class of equipment and methods utilize measurement of skin conductance for assessing the state of the autonomous nervous system of a patient, such as a sedated patient, e.g. for detecting pain or awakening during anaesthesia.

WO-03/094726 is an example of an apparatus and a method for monitoring the autonomous nervous system of a sedated patient, wherein the skin conductance, measured by use of electrodes placed on the skin of the patient, is measured. Signals indicating pain/discomfort in the patient and awakening in the patient are derived from the skin conductance measurements.

Medical electrode patches are often fixed to the skin by means of an adhesive. It is well known that the use of adhesive directly on the skin may result in an irritation of the patient's skin. This is particularly significant in the case of neonatal or preterm infants, since their skin is very vulnerable for adhesives.

When neonates are placed in an incubator, the humidity is particularly high. In such humid environments there is particularly difficult to make adhesive electrodes stick to the neonate's skin.

SUMMARY OF THE INVENTION

An object of the invention is to provide an improved electrode patch which may be advantageously used with infants or other persons/patients with sensible skin, in particular in humid environments.

The invention is set forth in the appended claims.

BRIEF DESCRIPTION OF THE DRAWINGS

Embodiments, aspects and principles of the invention will now be described in more detail with reference to the attached drawings, in which.

DETAILED DESCRIPTION

Figure 1:
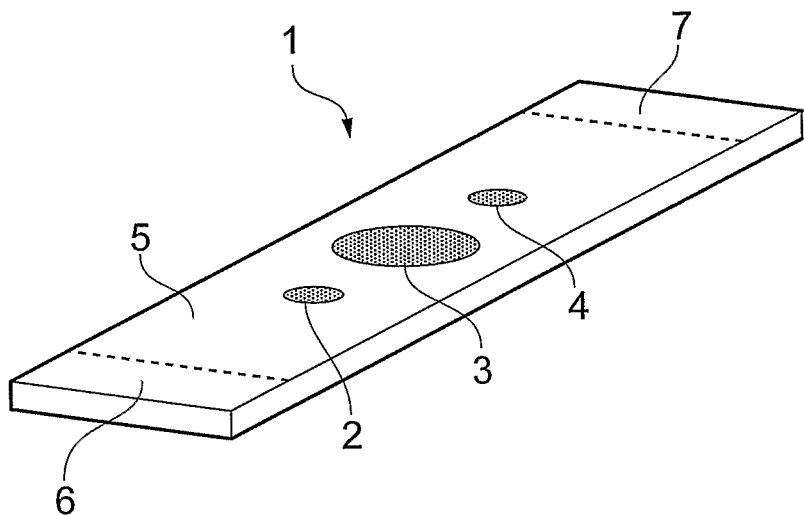
FIG. 1 is a schematic block diagram illustrating an electrode patch before it is attached to a body part of a patient.

FIG. 1 is a schematic block diagram illustrating a disposable electrode patch in accordance with the invention, in a state before it is attached to a body part of a patient.

The electrode patch 1 comprises a first conductive electrode 2, a second conductive electrode 3 and a third conductive electrode 4, all arranged in a flexible, elongated, non-conductive substrate. The substrate has a first surface 5 and a second, opposite surface (not visible on FIG. 1).

The substrate 5 has an elongated shape, e.g. a substantially rectangular shape as illustrated. Alternatively, the shape may be rectangular with rounded corners, oval, or any other suitable shape.

A first adhesive material is disposed on a first adhesive area 6 at a first end of the first surface.

Likewise, a second adhesive material is disposed on a second adhesive area 7 at a second end of the first surface.

Any known pressure sensitive adhesive (self stick, sticky adhesive) may be used.

A number of electrodes are arranged between the first and second adhesive areas on the first surface of the substrate. The electrodes may be of the type known as Ag/AgCl electrodes, although other types may alternatively be used.

Such an arrangement allows the electrode patch to be folded around a body part in such a way that the electrodes on the first surface make contact with the skin of the body part. Also, the first and second adhesive areas of the first surface are allowed to be pinched together to form a stable assembly surrounding the body part. This is further illustrated in FIG. 2.

The arrangement of attaching the electrode patch ensures that the electrodes do not suffer from excessive, undesired movement, which might lead to artefacts in the resulting measurements.

Moreover, direct contact between adhesive and the skin is avoided or significantly reduced.

In addition, the attachment of two adhesive patch areas together makes a firm and stable connection even in a humid environment such as, e.g., inside an incubator.

The area of the first surface, except from the first and second adhesive areas, may be non-adhesive. This will reduce the adhesive's possible unfavourable or irritating effect on the skin of the body part.

The substrate may comprise a foam material or another flexible material.

The electrodes may be covered with a layer of an electrode paste. The electrode paste may be prepared as a part of the disposable electrode patch. Alternatively, the electrode paste may be applied before use.

In an aspect, the first electrode 2 is a counter current electrode, the second electrode 3 is a measuring electrode, and the third electrode 4 is a reference voltage electrode. In use, the first electrode 1 may be electrically connected to a first connecting line (not shown) Similarly, the second electrode 2 may be electrically connected to a second connecting line (not shown). Similarly, the third electrode 4 may be electrically connected to a third connecting line (not shown).

The shapes, sizes and numbers of electrodes 2, 3, 4 may vary in accordance with the intended use of the electrode and other circumstances. In an aspect, there are three electrodes in the electrode patch.

Figure 2:
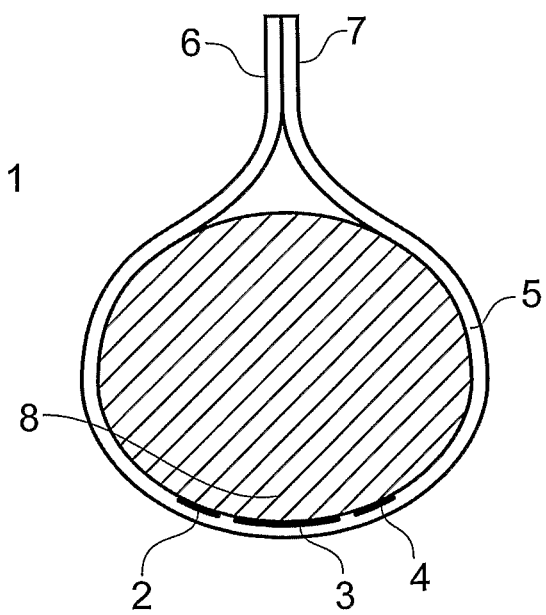
FIG. 2 is a schematic block diagram illustrating an electrode patch attached to a body part of a patient.

FIG. 2 is a schematic diagram illustrating the medical electrode patch attached to a body part 8 such as the plantar side of an infant's foot. Please refer to the description of FIG. 1 for a detailed description of those elements of FIG. 2 which are identical to (and have the same reference numerals as) those illustrated in FIG. 1.

The body part 8 may be a body part of an infant, including a preterm or a neonatal infant. However, the medical electrode patch may be used with body parts of any human or animal individual where it is necessary or desired to attach a medical electrode patch to the skin.

The body part 8 may be the plantar side of a foot or heel, or the palm of a hand, or any other suitable body part.

As will be realized, the electrode patch is allowed to be folded around the body part 8 in such a way that the electrodes 2, 3, 4 on the first surface make contact with the skin of the body part 8. Further, the first and second adhesive areas of the first surface are pinched (or pressed) together to form a tight and stable assembly surrounding the body part 8.

The medical electrode patch as disclosed in any of the above figures may e.g. be used in an arrangement for measuring skin conductance, e.g. of a patient.

In such use, the electrode patch 1 may be placed attached to an area of the skin on a body part of the patient, in such a way that is described above with reference to FIG. 2, for the purpose of measuring the skin's conductance at that area.

The first electrode 2 may a counter current electrode, the second electrode 3 may be a measuring electrode, and the third electrode 4 may be a reference voltage electrode, all arranged in the patch 5, which is placed on the skin area and attached by the attachment means described herein.

The electrode patch 1 and its connected external equipment may ensure a constant application of voltage over the stratum corneum (the surface layer of the skin) under the measuring electrode. The resulting current in a closed circuit between the measuring electrode 3 and the counter current electrode 2 may be measured by means of a measurement converter (not shown), connected between the counter current electrode 2 and the measuring electrode 3. The measurement converter may comprise a current to voltage converter, such as a transresistance amplifier or simply a resistance, which converts the current from the measuring electrode 3 to a voltage.

The electrode patch disclosed herein may also be used in an arrangement for monitoring the autonomous nervous system of a patient. Such monitoring may be non-diagnostic.

In this case a similar arrangement is used as explained above. In addition, the measuring equipment is connected to a processing device configured for monitoring the autonomous nervous system of the patient, based on measurements of the skin conductance. An example of suitable processing and monitoring means/methods has been disclosed in WO-03/094726 (expressly incorporated by reference).

Figure 3:
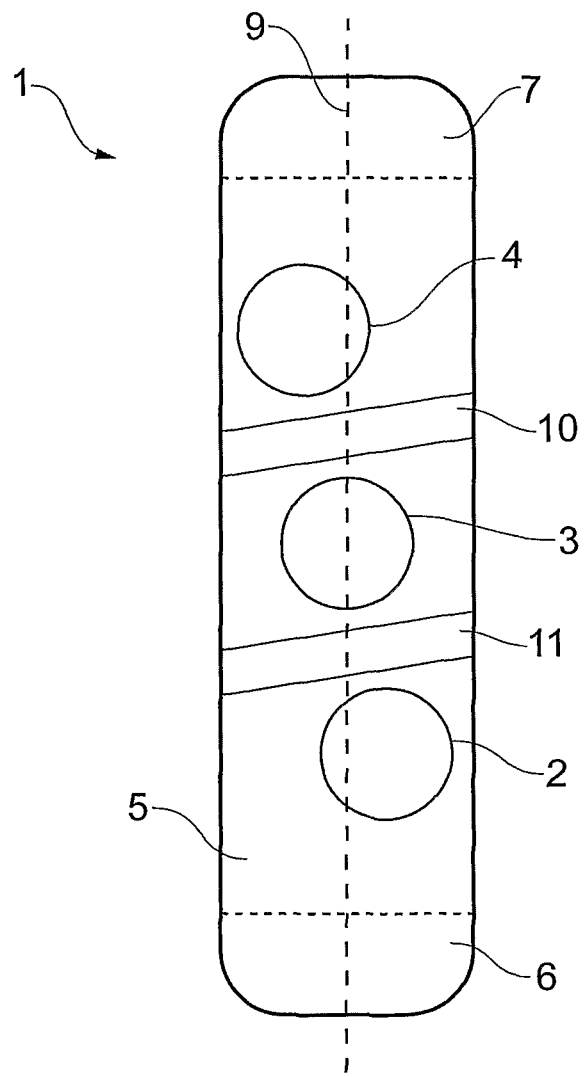
FIG. 3 is a schematic block diagram illustrating an embodiment of an electrode patch before it is attached to a body part of a patient.

FIG. 3 is a schematic block diagram illustrating an embodiment of an electrode patch before it is attached to a body part of a patient.

In a manner corresponding to the embodiment shown in FIG. 1, the electrode patch 1 comprises a first conductive electrode 2, a second conductive electrode 3 and a third conductive electrode 4, all arranged in a flexible, elongated, non-conductive substrate. The substrate has a first surface 5 and a second, opposite surface (not visible on FIG. 3). The electrodes comprise a counter current electrode, a measuring electrode and a reference voltage electrode. More specifically, the first electrode 2 is a counter current electrode, the second electrode 3 is a measuring electrode, and the third electrode 4 is a reference voltage electrode. Electrical connections may be provided in the same way as in the embodiment described above with reference to FIG. 1.

The substrate 5 has an elongated shape, e.g. a substantially rectangular shape with rounded corners, as illustrated. Other shapes are possible, as described earlier.

A first adhesive material is disposed on a first adhesive area 6 at a first end of the first surface and, a second adhesive material is disposed on a second adhesive area 7 at a second end of the first surface.

In the embodiment of the electrode patch as shown in FIG. 3, the counter current electrode 2 and the reference voltage electrode 4 are arranged with their centers on opposite sides of a line 9 which is parallel with the elongated substrate and which intersects a center of the measuring electrode 3. It should be understood that the line 9 does not need to be realized as a physical line. Rather, this line has been included in the present specification for the purpose of defining the relative positions of the various electrodes in the electrode patch.

The counter current electrode 2, the measuring electrode 3 and the reference voltage electrode 4 may have a substantially circular shape, as shown. Other shapes are possible.

The above-mentioned line which is parallel with the elongated substrate, and which intersects the center of the measuring electrode 3, may also intersect an area of each of the counter current electrode 2 and the reference voltage electrode 4, as illustrated in FIG. 3.

Alternatively, the line which is parallel with the elongated substrate, and which intersects the center of the measuring electrode, does not intersect any one of the counter current electrode 2 or the reference voltage electrode 4, or the line may intersect only one of the counter current electrode 2 and the reference voltage electrode 4.

In the embodiment shown in FIG. 3, the areas of the counter current electrode 2, the measuring electrode 3 and the reference voltage electrode 4 are the same or substantially the same. In other embodiments, the areas may be different. For instance, in the embodiment of FIG. 1, the measuring electrode 3 is substantially larger than the counter current electrode 2 and the reference voltage electrode 4.

FIG. 3 further shows a slanted strip area 10 between the reference voltage electrode 4 and the measuring electrode 3, and a similar slanted strip area 11 between the measuring electrode 3 and the counter current electrode 2. In an aspect, electrode paste is applied not only to the electrodes 2, 3, and 4, but also to the rhomb- or parallelogram-shaped areas surrounding each electrode 2, 3, 4. However, in an aspect, electrode paste is not applied to the slanted strips 10, 11. Also, in an aspect, electrode paste is not applied to the adhesive areas 6 and 7.

In an aspect, where the electrode patch is manufactured with pre-applied electrode paste, electrode paste may be pre-applied on the entire surface 5 of the patch except from the adhesive areas 6 and 7 and the slanted strips 10, 11.

Further possible values and specifications of the electrode patch and its elements are given below (for illustration, not for limitation):

Area of the central electrode 3: between 100 mm$^2$ and 400 mm$^2$, more specifically, between 200 mm$^2$ and 300 mm$^2$, e.g. about 260 mm$^2$.

Area of the outer electrodes 2, 4: between 30 mm$^2$ and 250 mm$^2$, more specifically, between 70 mm$^2$ and 150 mm$^2$, e.g. about 100 mm$^2$.

Alternatively, the central electrode 3 may have the same or approximately the same area as each of the outer electrodes.

Distance between electrodes: between 0.2 mm and 3 mm, more specifically, between 0.5 mm and 1.2 mm, e.g. about 0.7 mm.

Alternatively, e.g. in the case of slanted strip areas on which electrode paste is not applied, the distance between electrodes (i.e., distance between outer edge of subsequent electrodes) may be between 2 mm and 8 mm, more specifically, between 4 and 6 mm, e.g., about 5 mm.

Total length of patch: between 40 mm and 120 mm, more specifically, between between 60 mm and 100 mm, e.g. about 80 mm.

Total width of patch: between 10 mm and 30 mm, more specifically, between 15 mm and 25 mm, e.g. about 20 mm.

Thickness of patch: between 0.5 mm and 2 mm, more specifically, between 0.8 mm and 1.5 mm, e.g. about 1.0 mm.

Length of first 6 and second 7 adhesive areas (measured in longitudinal direction of the elongated patch): between 5 mm and 20 mm, more specifically, between 8 mm and 15 mm, e.g. about 10 mm.

Length of slanted strip area: between 2 and 6 mm, more specifically, between 3 and 5 mm, e.g. about 4 mm.

An electrode paste useful for application with the electrode patch may, as an example, have the following composition:

6 g hydroxyethylcellulose 700, 0.58 g NaCl, 0.1 g methylparahydroxybenzene, 0.1 g propylparahydroxybenzene, 2 g alcohol 96%, and purified water up to 100 g. Electrode pastes with other compositions may alternatively be used.

The skilled person will readily realize that dimensions may be altered in order to meet varying circumstances, such as various sizes of the body part.

The inventive concept is not limited to the exemplary embodiments described—above. Rather, the scope of the invention is set forth in the following patent claims.

The invention claimed is:

1. Disposable electrode patch for medical purposes, comprising
    a flexible, elongated substrate with a first and a second surface,
    a first adhesive material disposed on a first adhesive area at a first end of the first surface, and
    a second adhesive material disposed on a second adhesive area at a second end of the first surface, and
    a number of electrodes arranged between the first and second adhesive areas on the first surface of the substrate, thus allowing the electrode patch to be folded around a body part in such a way that the electrodes on the first surface make contact with the skin of the body part, further allowing the first and second adhesive areas of the first surface to be pinched together to form a stable assembly surrounding the body part,
    wherein the electrodes comprise a counter current electrode, a measuring electrode and a reference voltage electrode, and
    wherein the counter current electrode and the reference voltage electrode are arranged with their centers on opposite sides of a line which is parallel with the elongated substrate and which intersects a center of the measuring electrode,
    wherein each of the counter current electrode, the measuring electrode and the reference voltage electrode have a substantially circular shape, and
    wherein said line which is parallel with the elongated substrate, and which intersects the center of the measuring electrode, also intersects an area of each of the counter current electrode and the reference voltage electrode.

2. Disposable electrode patch according to claim 1, wherein the substrate comprises a foam material.

3. Disposable electrode patch according to one of the claim 1-2, wherein the electrodes are prepared with a covering layer of an electrode paste.

4. Disposable electrode patch according to claim 3, wherein the area of the first surface, except from the first and second adhesive areas, is non-adhesive.

5. Disposable electrode patch according to claim 1, wherein the body part is a body part of an infant, including a preterm or a neonatal infant.

6. Disposable electrode patch according to claim 5, wherein the body part is the plantar side of a foot or heel, or the palm of a hand.

\* \* \* \* \*